United States Patent [19]
Forat et al.

[11] Patent Number: 5,859,288
[45] Date of Patent: Jan. 12, 1999

[54] REAGENT AND PROCESS FOR THE SYNTHESIS OF OXYSULPHIDE-CONTAINING FLUORINE-CONTAINING ORGANIC DERIVATIVES

[75] Inventors: Gerard Forat, Lyons; Jean-Manuel Mas, Millery; Laurent Saint-Jalmes, Meyzieu, all of France

[73] Assignee: Rhone-Poulenc Chimie, Courbevoie Cedex, France

[21] Appl. No.: 620,359

[22] Filed: Mar. 22, 1996

[30] Foreign Application Priority Data

Mar. 24, 1995 [FR] France ................................. 95 03515
Dec. 29, 1995 [FR] France ................................. 95 15764

[51] Int. Cl.$^6$ ................................. C07C 313/02
[52] U.S. Cl. ................... 562/113; 502/118; 502/125; 502/827; 502/829
[58] Field of Search .................. 562/113, 125, 562/118, 827, 829

[56] References Cited

FOREIGN PATENT DOCUMENTS 165135   12/1958   European Pat. Off. .
2593808   8/1987   France .
2660923  10/1991   France .

OTHER PUBLICATIONS

Journal of Organic Chemistry, vol. 54. No. 10, 12 May. 1989, Washington, D.C., USA, pps. 2452–2453, M. Tordeux, et al.: 'Reactions of bromotrifluoromethane and Related halides. 8. Condensations with dithionite and hydroxymethanesulfinate salts. '.

Journal of Fluorine Chemistry, vol. 45, No. 3 Dec. 1989, Lausanne, Ch, pps. 431–433, G.P. Stahly; 'Trifluoromethylation of 1,3,5–Trinitrobenzen.'.

*Primary Examiner*—Robert Gerstl
*Attorney, Agent, or Firm*—Burns, Doane, Swecker & Mathis, L. L. P.

[57] ABSTRACT

The invention relates to a reagent which is useful for the synthesis of oxysulphide-containing fluorine-containing organic derivatives by reacting with an oxide of sulphur, especially sulphur dioxide, characterized in that it comprises:

a) a fluorocarboxylic acid of formula $E_w$—$CF_2$—COOH where $E_w$ is an electron-withdrawing group or atom which is at least partially salified by an organic or inorganic cation, and b) an aprotic polar solvent; and in that the content of releasable protons carried by its various components, including their impurities, is at most equal to half the initial molar concentration of the said fluorocarboxylic acid.

This reagent can be used by heating in order to form fluorine-containing sulphinic or sulphonic acids.

19 Claims, No Drawings

REAGENT AND PROCESS FOR THE SYNTHESIS OF OXYSULPHIDE-CONTAINING FLUORINE-CONTAINING ORGANIC DERIVATIVES

The present invention relates to a process for the preparation of fluoroalkanesulphinic and sulphonic acids and their salts.

It relates more particularly to the preparation of polyhalosulphinic and sulphonic, especially difluoro- or trifluoromethanesulphinic and sulphonic, acids.

Perhaloalkanesulphonic acids and more particularly trifluoromethanesulphonic acid are used as catalysts or as intermediates in organic synthesis.

Initially, the only known process for the manufacture of trifluoromethanesulphonic acid was electrochemical fluorination as described especially by R. D. Howels, J. D. McCown in Chemical Reviews, 1977, 77, 69.

The process for the preparation of trifluoromethanesulphinic acid, which is described in the European patent published under the number EP-165 135, is also known which consists in exposing to sulphur dioxide a metal selected from zinc, aluminium, manganese, cadmium, magnesium, tin, iron or even nickel and cobalt, in an aprotic polar solvent and then in adding a trifluoromethyl halide at a pressure greater than $10^5$ Pa. This process makes it possible to obtain a product in the form of trifluoromethanesulphinate with good yields. The sulphinate obtained is present in a medium containing a large quantity of zinc salt. The separation of the sulphinate and the other zinc salts poses, at the industrial level, a problem which has to be solved.

Moreover, this technique, as well as the one described in the French Application published under the number 2,593,808, required the use of perfluoroalkyl bromides which are reputed to be particularly harmful for the atmospheric layers, especially because of their high greenhouse effect and their reputedly damaging effect on ozone.

Accordingly, one of the aims of the present invention is to provide a reagent for the preparation of oxysulphide-containing fluorine-containing organic derivatives, by reacting with an oxide of sulphur, which makes it possible to us products which are less harmful for the environment than trifluoromethyl bromide while remaining low in price.

Attempts have often been made to use as source of perfluoroalkyl radicals, more generally of trifluoromethyl radicals, perfluorocarboxylic acids, by using decomposition reactions intended to remove the carboxylic fragment from the said acids while releasing carbon dioxide. However, the successes which had been achieved were highly mitigated and used particularly complicated catalytic systems. The perfluoroalkyl radicals or their equivalents generated by the decomposition of the said perfluorocarboxylic acids were, in addition, unstable in the reaction medium and required the use of stabilizing agents.

The present invention is intended to overcome the disadvantages of the existing processes by providing a reagent which is more environmentally friendly and capable of giving the desired products with a satisfactory yield.

During the study which led to the present invention, it was demonstrated that it was possible to generate fluoroalkyl radicals from a fluorocarboxylic acid, without a catalyst and without an agent capable of stabilizing the various envisaged intermediates obtained during the decomposition of the different perfluorocarboxylic acids.

It appeared that, in order to obtain in this manner decarboxylation of the fluorocarboxylic acids, two conditions were essential; one is the choice of the solvent, the other the impurity content of the mixture constituting the reagent according to the present invention. Thus, it was possible to demonstrate the absolutely critical role of the labile hydrogen atoms content of the system, or more precisely the releasable protons content, which should be less than the content of fluorine-containing groups released by the decomposition of the fluorocarboxylic acids. Labile hydrogen atom or releasable proton is understood to mean a hydrogen atom which is capable of being removed in the form of a proton by a strong base. In practice, the protons of acidic functional groups which have a pKa of less than about 20 are involved ("about" is used to emphasize that the number 20 has only one significant figure).

The abovementioned aims, and others which will appear later, are therefore achieved by means of a reagent which is useful for the synthesis of oxysulphide-containing fluorine-containing organic derivatives by reacting with an oxide of sulphur, especially sulphur dioxide, characterized in that it comprises:

a) a fluorocarboxylic acid of formula $E_w$—$CF_2$—COOH where $E_w$ is an electron withdrawing group or atom which is at least partially salified by an organic or inorganic cation, and b) an aprotic polar solvent; and in that the content of releasable protons carried by its various components, including their impurities, is at most equal to half the initial molar concentration of the said fluorocarboxylic acid.

The greater the content of releasable protons, the lesser the risk of interfering reaction and the better the yield.

Thus, it is preferable that, in the reagent, the content of labile hydrogen atoms is at most equal to 10%, preferably to 1% (by mol), relative to the initial content of the said fluorocarboxylic acid.

The principal impurity, which carries labile hydrogen atoms, is in general water which is capable of releasing up to two protons per molecule.

In general, it is preferable to use carefully dehydrated reagents and solvents so that the water content by weight of the reagent is at most equal to 1 per 1000, relative to the total mass of the reagent. Depending on the reaction conditions as a whole, such water contents may be satisfactory, but in some cases, it may be advantageous to carry out the procedure at lower levels, for example of the order of 1 per 10,000.

However, it is not necessarily essential to remove all the water and a water/fluorocarboxylic acid molar ratio of less than 10% may be tolerated.

Moreover, it has been possible to show that other elements, namely transition elements having two stable valency states, such as copper, may not be good, or may be even detrimental to the invention.

Although this reagent according to the invention does not require a catalyst, such metallic elements may be present as impurities provided especially by the solvent.

Thus, it is preferable that the molar content of these elements is less than 1000, advantageously less than 100, preferably less than 10 ppm relative to the initial content of the said fluorocarboxylic acid.

In order to favour certain substrates and to favour certain types of reaction, it has also been recommended many times to use with perfluoroacetic acid elements from column VIII in the periodic classification of the elements. This proved to be of no interest for the intended reaction above. Accordingly, taking into account the high price of these compounds, it is preferable to use reagents not containing column VIII metals, especially metals of the platinum ore which is the group consisting of platinum, osmium, iridium, palladium, rhodium and ruthenium.

In the present description, reference is made to the supplement to the bulletin of the Chemical Society of France number 1, January 1966, where a periodic classification of the elements has been published.

Thus, it is preferable that the content of platinum ore metals, or even of column VIII metals, is less than 100 ppm, advantageously less than 10 ppm, preferably less than 1 ppm. These values are expressed relative to the starting fluorocarboxylic acid and are expressed in mol.

In a more general and more empirical manner, it can be stated that these two categories of metals, namely the transition elements with two valency states and the column VIII elements, should be present in the reagent at an overall concentration level at most equal to 1000 molar ppm, preferably to 10 molar ppm.

It will be noted that the different metals present at such an overall concentration level are in an extremely small quantity, and in this regard, they play no catalytic role. Their presence does not enhance the kinetics of the reaction or is even detrimental to it when they are present in an excessively large quantity.

The use, in addition to the abovementioned reagent components, of an alkali metal fluoride or of a quaternary ammonium fluoride, which are usually present in the reactive systems using fluorine-containing carboxylates, did not prove detrimental, but it proved to be of little value, because of the fact that it produces saline effluents which are difficult to treat.

It can be noted, however, that the presence of fluorides in the medium tends to limit both the conversion of the starting fluorocarboxylic acid and the decomposition of the end product. Overall, this effect is rather positive, in favour of a better yield of conversion of fluorocarboxylic acid to the desired product, that is to say a good selectivity of the reaction.

The bulkier the countercation for the fluoride, the more this effect tends to be significant. Cations which may be envisaged are the cations of alkali metals whose rank is above that of sodium, in particular potassium or caesium, or alternatively the "onium" type ions, namely cations formed by the elements of columns V B and VI B (as defined in the periodic table of the elements published in the supplement to the bulletin of the Chemical Society of France in January 1966), with 3 or 4 hydrocarbon chains.

Among the oniums which are derived from group V B elements, the preferred reagents are the tetraalkyl or tetraaryl ammoniums or phosphoniums. The hydrocarbon group comprises advantageously from 4 to 12 carbon atoms, preferably from 4 to 8 carbon atoms. The oniums which are derived from column VI B are preferably derived from elements with an atomic number greater than that of oxygen.

In spite of the disadvantages which have been mentioned above, the content of fluoride ions is a parameter which can be considered. It may, however, be preferable to limit this content, in particular the initial content, in order to facilitate the final treatment of the reaction medium. Thus, it is advantageous that the fluoride content, which is qualified as being ionic that is to say capable of being ionized in the polarizing medium of the reagent, is at most equal to the initial molar concentration of the said fluorocarboxylic acid salt, advantageously to half, preferably to a quarter.

As mentioned above, the solvent plays an important role in the present invention and should be aprotic, and advantageously polar and should contain very few impurities carrying acidic hydrogen.

It is thus preferable that the aprotic polar solvent which can be used has a significant dipolar moment. Thus, its relative dielectric constant $\epsilon$ is advantageously at least equal to about 5 (the positional zeros are not considered to be significant figures in the present description unless otherwise stated). Preferably, $\epsilon$ is less than or equal to 50 and greater than or equal to 5, and is especially between 30 and 40.

It is preferable, in addition, that the solvents of the invention are capable of satisfactorily solvating the cations, which can be coded using the donor number DN of these solvents. It is thus preferable that the donor number DN of these solvents is between 10 and 30. The donor number corresponds to $\Delta H$ (variation of enthalpy), expressed in kilocalorie per mol, of the combination of the said aprotic polar solvent with antimony pentachloride.

According to the present invention, it is preferable that the reagent does not have any acidic hydrogen on the polar solvent(s) which it uses. In particular, when the polar character of the solvent(s) is obtained by the presence of electron withdrawing groups, it is desirable that there is no hydrogen at the alpha position relative to the electron-withdrawing functional group.

In general, it is preferable that the pKa corresponding to the first acidity of the solvent is at least equal to about 20 ("about" emphasizing that only the first figure is significant), advantageously at least equal to about 25, preferably between 25 and 35.

The acidic character can also be expressed by the acceptor number $A_N$ of the solvent, as defined by Reichardt, "Solvents and solvent effects in Organic Chemistry", 2nd edition, VCH (Germany), 1990, pages 23–24. Advantageously, this acceptor number $A_N$ is less than 20, in particular less than 18.

It is preferable that the said acid or salt of fluorocarboxylic acid is at least partially, preferably completely, soluble in the medium constituting the reagent.

The solvents which give good results may be especially amide-type solvents. Among the amides, there are also included the amides with a specific character such as tetra-substituted ureas and monosubstituted lactams. The amides are preferably substituted (disubstituted for the ordinary amides). There may be mentioned for example pyrrolidone derivatives, such as N-methylpyrrolidone, alternatively N,N-dimethylformamide, or N,N-dimethylacetamide.

Also advantageous are solvents such as 1,3-dimethyl-3,4,5,6-tetrahydro-2(1H)pyrimidinone (DMPU), 1,3-dimethyl-2-imidazolidinone (DMI or DMEU), or benzonitrile.

Another particularly advantageous category of solvent consists of ethers, whether they are symmetrical or not symmetrical, whether they are open or not. In the category of ethers, there should be incorporated the different derivatives of glycol ethers such as the different glymes, diglyme for example.

In the fluorocarboxylic acid of the constituent a) of the reagent of the invention, the entity E which exerts an electron withdrawing effect on the difluorinated carbon atom is preferably selected from the functional groups whose Hammett constant $\sigma_p$ is at least equal to 0.1. It is, in addition, preferable that the inductive component of $\sigma_p$, $\sigma_i$, is at least equal to 0.2, advantageously to 0.3. In this regard, reference can be made to the book by March, "Advanced Organic Chemistry", third edition, John Wiley and Son, pages 242 to 250, and especially in table 4 of this section.

More particularly, the electron-withdrawing entity $E_w$ may be selected from halogen atoms, which are preferably light, especially chlorine and fluorine. The corresponding fluorocarboxylic acid is a halofluoroacetic acid of formula (1)

X—CF$_2$—COOH where X is a halogen atom, which is advantageously light (chlorine or fluorine).

E$^w$ may also be advantageously selected from nitrile groups (with the risk, as interfering reaction, of an alpha-elimination), carbonylated groups, sulphonated groups and perfluoroalkylated groups. Fluorocarboxylic acids of this type which can be used correspond to the formula (2) R—G—CF$_2$—COOH where R—G represents a nitrile group or alternatively G represents

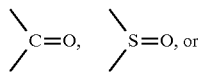

—(CF$_2$)$_n$— where n is greater than or equal to 1, and R represents any organic or inorganic residue, preferably an organic radical such as aryl, alkyl or aralkyl, which is optionally substituted. R may also represent an inorganic or organic solid support, such as a resin.

In the case where G represents a perfluoroalkylene group —(CF$_2$)$_n$—, n is advantageously between 1 and 10, preferably between 1 and 5. Still in this case, R may also represent a halogen atom, especially fluorine.

In general, except in the case where the fluorocarboxylic acid is a polymer, the total number of carbon atoms of the fluorocarboxylic acid advantageously does not exceed 50.

The countercations which are capable of forming a salt with the said fluorocarboxylic acid are advantageously bulky. Thus, alkali metal salts are preferred, advantageously where the said metal is selected from sodium, potassium, rubidium, caesium and francium. Preferably, the metal is of a period whose rank is at least equal to that of sodium, advantageously to that of potassium. Quaternary ammonium salts are also preferred.

It is also possible to enhance the reaction using cations which are, either naturally bulky such as the quaternary ammonium or quaternary phosphonium cations, or made bulky by the addition of chelating agents or preferably of cryptands, such as for example the crown ethers or the derivatives which are both aminated and oxygenated.

Salts of perfluorocarboxylic acids can be advantageously used, such as alkali metal, especially potassium, trifluoroacetate, perfluoropropionate and perfluorobutyrate.

It can be noted that the use of sequestrants of the crown ether type greatly accelerates the conversion of the starting fluorocarboxylic acid.

It will be possible to use such sequestrants advantageously in an amount of 5 to 100 mol %, especially 5 to 25 mol % relative to the initial fluorocarboxylic acid content.

However, it will be possible for certain combinations with other partners of the reaction medium, especially certain solvents, to have a less favourable effect as regards the stability of the end product, and they will not therefore be considered to be advantageous.

Another aim of the present invention is to provide a process for the synthesis of oxysulphide-containing fluorine-containing organic derivatives, especially of sulphinic or sulphonic acid salts, using the reagent according to the present invention.

This aim is achieved by:
a) exposing the said reagent to an oxide of sulphur and
b) heating the resulting mixture at a temperature of between 100° C. and 200° C., preferably of between 120° and 150° C., and this, for a period of at least half an hour, advantageously of at least one hour, and of at most one day, advantageously of less than 20 hours.

The exposure or the contacting of the reagent with the substrate may be gradual or otherwise. In particular, it is possible to wait for one of the two to be at the right temperature in order to introduce the other. This introduction may be gradual or otherwise. The reagent may be poured into the substrate or conversely. The fluorocarboxylate and the substrate may be introduced both simultaneously and gradually into the solvent.

When the said oxide is sulphur dioxide, the mixture resulting from step a) may comprise two phases in equilibrium and may thus contain a liquid phase, where at least part of the said acid or of the sulphur dioxide is dissolved in the said solvent, in equilibrium with a gaseous phase which contains sulphur dioxide.

As regards the relative quantities of the said initial fluorocarboxylic acid, and of oxide of sulphur, preferably dioxide, it is preferable that the ratio is between 1 and 10, advantageously around two, sulphur atoms per molecule of fluorocarboxylic acid.

It has been possible to observe that, all else being otherwise equal, the yield of organic derivative desired depends on the progress of the reaction and that a very low final yield can be obtained in spite of a substantial conversion of the reagents. Without wishing to be tied to any scientific theory, it appears that it all happens as if there was a kinetics of formation and a kinetics of degradation of the products obtained.

In order to avoid an excessive degradation of the final product, and therefore to ensure good selectivity of the reaction, it is preferable not to seek to completely convert the starting fluorocarboxylic acid. The progress of the reaction can be controlled by the rate of conversion (RC) of the acid which is the molar ratio of the quantity of acid which has disappeared to the initial quantity of acid in the reaction medium, this rate being easily calculated after assaying the acid remaining in the medium.

Advantageously, the reaction will be conducted only until a conversion rate of 40 to 80%, preferably of 50 to 70%, is obtained, then the reaction products are separated. It is possible to achieve in this manner a selectivity of the order of 80%, expressed by the molar ratio desired product/fluorocarboxylic acid converted.

In order to be under optimum reaction conditions, it is possible to limit the conversion rate by modifying both the duration of the reaction, the nature of the solvent and the presence of additives which tend to limit this conversion, such as fluoride ions for example. The kinetics of the reaction depend, in addition, on the reaction partners (fluorocarboxylic acid and oxide of sulphur) and it will be possible to easily adapt the appropriate reaction time on a case by case basis depending on this kinetics.

In the case of sulphur dioxide, a reaction time of 2 to 7 hours may be sufficient, depending on the reagent used.

Once the desired conversion rate has been achieved, the reaction mixture can be treated in a manner known per se in order to separate the product obtained, it being possible for the starting products to be recycled in order to produce an additional quantity of the desired organic derivative.

When the said oxide of sulphur is sulphur dioxide, the product obtained by heating the reagent is a sulphinic acid or a sulphinic acid salt whose counterion is that of the starting fluorocarboxylic acid salt.

To separate the reaction product, one advantageous possibility consists in carrying out an additional conversion to a relatively volatile and easily distillable derivative.

Thus, for example, during the reaction between SO$_2$ and the trifluoroacetic acid CF$_3$CO$_2$H or its salts, the trifluoromethylsulphinic acid CF$_3$SO$_2$H or its salts which are obtained can be easily converted in the presence of chlorine Cl$_2$ to the acid chloride corresponding to an oxidation, namely CF$_3$SO$_2$Cl (this is a general reaction for the acids used and especially for the perfluoroalkanesulphinic acids R$_f$SO$_2$H). This reaction, which does not affect the reagent based on trifluoroacetic acid, makes it possible advantageously to separate $CF_3SO_2Cl$ by distillation, leaving inorganic chlorides as well as the trifluoromethylation reagent intact in the reaction medium, which can therefore be reused in order to continue the reaction with the oxide of sulphur. This reaction is common to the different fluorine-containing sulphinic acids which can be obtained according to the invention. This example can be generalized to the separation of all types of fluorine-containing oxysulphide-containing organic derivatives obtained according to the invention which are capable of being converted by an appropriate reaction to more volatile products.

To pass from the sulphinic acid to the corresponding sulphonic acid, the reaction product or the purified reaction product should be subjected to an oxidation, which is known per se, especially by means of hydrogen peroxide or sodium hypochlorite. A process for the purification of sodium trifluoromethylsulphinate, and for oxidation to the sulphonate, which is applicable according to the invention, is described in the European patent application published under the number EP-A-0,396,458.

The sulphinic or sulphonic acid salts thus obtained can be converted to the corresponding free acids in an acid medium.

The reaction products, salts or free acids, can be easily isolated and used in subsequent organic synthesis steps. Thus, for example, it is possible to enhance the value of the sulphinyl chlorides obtained from fluorine-containing sulphinic acids prepared according to the invention.

The following nonlimiting examples illustrate the invention.

The results presented in the examples are expressed as a function of three parameters which are defined below:

the rate of conversion of a reagent R (RCR) is the ratio of the molar quantity of R which has disappeared during a reaction over the initial quantity of R;

the actual yield of production of a product P from a reagent R ($A^{YP}$) is the ratio of the quantity of P produced to the initial quantity of R;

the yield of conversion of R to P (YCP) which is the ratio of the quantity of P produced over the quantity of R which has disappeared.

EXAMPLE 1

Preparation of trifluoromethylsulphinic acid 42 g of N-methylpyrrolidone (NMP) are introduced into a 100 ml Hastalloy reactor, stirred by a turbine, followed by 5.32 g (35 mmol) of potassium trifluoroacetate and finally 4.9 g (76 mmol) of sulphur dioxide gas by bubbling in the liquid. The sulphur dioxide is completely solubilized by the NMP.

The molar ratio of the sulphur dioxide to the potassium trifluoroacetate is 2.1.

The water content of the reactive mixture is 0.1% by weight relative to the weight of the mixture, that is to say a molar ratio of water to trifluoroacetate of 0.07.

The mixture is heated in the closed reactor at a temperature of 140° C. for 6 hours, with stirring.

During the reaction, the internal pressure of the reactor, expressed in terms of room temperature, increases by $3.5 \times 10^5$ Pa relative to the initial pressure.

The reaction medium is then taken up in water and analysed by ionic chromatography HPIC (High Performance Ionic Chromatography) in separating mode in order to determine the conversion of the potassium trifluoroacetate.

The rate of conversion (RC) of the starting potassium trifluoroacetate, expressed by the molar ratio of the quantity of trifluoroacetate consumed (converted) to the initial quantity, is 61.7%.

The actual yield (AY) expressed by the molar ratio of the quantity of trifluoromethylsulphinate formed, in free or salified form, to the initial quantity of trifluoroacetate, is 29.7%.

The yield relative to the converted product (YC), expressed by the molar ratio of the quantity of trifluoromethylsulphinate formed, in free or salified form, to the quantity of trifluoroacetate converted, is 48.1%. The product is isolated in the form of a potassium salt.

EXAMPLE 2

Example 1 is repeated exactly, except that 8.6 g (35 mmol) of caesium trifluoroacetate are used in the reagent.

The HPIC assay makes it possible to calculate that RC is equal to 68.4%, At is equal to 21% and YC is equal to 30.7%. The product is isolated in the form of a caesium salt.

The use of caesium trifluoroacetate is relatively less advantageous than the potassium salt.

EXAMPLES 3 and 4

Example 1 is repeated exactly, except that N,N-dimethylacetamide (DMAC, $\epsilon$=37.8) and N,N-dimethylformamide (DMF, $\epsilon$=36.7) are used as solvent, respectively.

The progress of the reaction is determined by HPIC and the results are reported in Table 1, where the solvent used and its donor number DN are stated as a reminder, for each example.

Comparative Example 1

Example 1 is repeated exactly, except that the procedure is carried out only in the presence of an excess of sulphur dioxide without solvent (dielectric constant $\epsilon$=14).

The results are presented in Table 1.

TABLE 1

| Example | Solvent | DN | RC | AY | YC |
|---------|---------|------|------|------|------|
| Ex 1 | NMP | 27.3 | 61.7 | 29.7 | 48.1 |
| Ex 3 | DMAC | 27.8 | 78.6 | 40.6 | 51.7 |
| Ex 4 | DMF | 26.6 | 80.4 | 33.8 | 41.7 |
| Comp Ex 1 | — $(SO_2)*$ | — | 9 | 0 | 0 |

*$SO_2$ serves both as solvent and reagent.

The Comparative Example 1 shows that the solvent is necessary for the conversion to the desired product.

EXAMPLE 5

This example summarizes a series of other tests where various solvents were tested under conditions similar to those of Example 1.

The potassium trifluoroacetate (in a $CF_3CO_2K$/solvent weight ratio=0.13) is exposed to about 2 molar equivalents of sulphur dioxide ($SO_2/CF_3CO_2K$ molar ratio of 1.9 to 2.1).

The mixture of reagents is heated in a closed reactor stirred at 1000 rpm with a temperature rise of 10° C./min up to 140° C., for 6 h.

The progress of the reaction is determined by HPIC and the results are presented in Table 2 where the solvent used, its dielectric constant $\epsilon$, its donor number DN, its acceptor number AN and the water content in the medium are stated as a reminder for each test.

TABLE 2

| Test | Solvent | ε | DN | AN | $H_2O/CF_3CO_2K$ mol % | RC (%) | AY $CF_3SO_2K$ (%) | AY $F^-$ (%) | YC $CF_3SO_2K$ (%) |
|---|---|---|---|---|---|---|---|---|---|
| a | DMSO | 48.9 | 29.8 | 19.3 | 4 | 26.6 | 4.6 | — | 17.3 |
| b | $CH_3CN$ | 38 | 14.1 | 18.3 | 1.6 | 12.6 | 3 | 3 | 23.8 |
| c | DMF | 36.7 | 26.6 | 16.0 | 1 | 73.5 | 41.8 | 10.9 | 56.9 |
| d | NMP | 32.2 | 27.3 | 13.3 | 1.6 | 67.2 | 27.9 | 25.1 | 41.5 |
| e | Benzonitrile | 25.2 | 11.9 | 15.5 | 1.5 | 22.1 | 7.4 | 3.6 | 33.5 |
| f | DMPU | 36.1 | / | / | 1.5 | 82.1 | 42.9 | 9.8 | 52.3 |
| g | DMAC | 37.8 | 27.8 | 13.6 | 1.9 | 74 | 43.3 | 3 | 58.6 |
| h | Anisole | 4.3 | / | / | 1.2 | 21.6 | 4.4 | 3 | 20.4 |
| i | Xylene | 2.4 | / | / | 0.4 | 23.2 | 4.4 | 3 | 19 |
| j | Diglyme | 5.7 | / | 9.9 | 1.9 | 28.4 | 15.6 | 3 | 54.9 |
| k | DMI (DMEU) | 37.6 | / | / | 1.4 | 66.1 | 47.5 | 7.4 | 72 |

In general, for the solvents which are not very acidic (AN<19), the yields vary in the same direction as the dielectric constant ε. In this regard, the DMF, DMAC and DMPU give excellent results, those of NMP being slightly lower.

On the other hand, with DMSO and $CH_3CN$, the results are less good, in spite of high dielectric constants, and this is caused by their acidic character (AN=19.3).

EXAMPLE 6

Example 1 is repeated exactly, except that more carefully dehydrated reactive compounds are used. The water content in the reactive mixture is 0.05% by weight relative to the weight of the mixture, that is to say a water to trifluoroacetate molar ratio of 0.04. The results of the test, determined by HPIC, are presented in Table 3. The results of Example 1 are also given in the Table as a reminder.

Comparative Example 2 (to be compared with Examples 1 and 6)

In contrast to the preceding example, Example 1 is repeated with more hydrated reagents, such that the content of releasable protons is outside the limits of the invention. The water content in the reactive mixture is 0.8% by weight relative to the weight of the mixture. The water to trifluoroacetate molar ratio is 0.6, the ratio of the content of releasable protons provided by the water to the content of trifluoroacetate is therefore 1.2. The results of the test, determined by HPIC, are presented in Table 3.

EXAMPLE 7

Example 6 is repeated exactly, except that DMAC is used as solvent.

The results of the test are presented in Table 3, where the results of Example 3 are also presented.

TABLE 3

| Example | $H_2O$ (% by weight) | $H_2O/CF_3COOK$ (mol/mol) | RC (%) | AY (%) | YC (%) |
|---|---|---|---|---|---|
| Ex 1 | 0.1 | 0.07 | 61.7 | 29.7 | 48.1 |
| Ex 6 | 0.05 | 0.04 | 64 | 54 | 85 |
| Comp Ex 2 | 0.8 | 0.6 | 100 | 0 | 0 |
| Ex 3 | 0.1 | 0.07 | 78.6 | 40.6 | 51.7 |
| Ex 7 | 0.05 | 0.04 | 68 | 47 | 69 |

Examples 6 and 7 show that a low water content remarkably enhances the yield of conversion.

The Comparative Example 2 confirms that a releasable proton content of the reactive system greater than half the content of trifluoroacetic acid salt is detrimental to the reaction for the formation of the trifluoromethylsulphinate.

EXAMPLE 8

This example summarizes a series of tests which also demonstrate the importance of the water content in the reaction of the sulphur dioxide with the potassium trifluoroacetate under conditions similar to those of Example 1.

Still in NMP, the potassium trifluoroacetate (in a weight ratio relative to the solvent $CF_3CO_2K/NMP=0.13$) is exposed to about 2 molar equivalents of sulphur dioxide ($SO_2/CF_3CO_2K$ molar ratio of 1.9 to 2.1).

The mixture is heated in the closed reactor stirred at 1000 rpm with a temperature rise of 10° C./min up to 140° C. for 6 hours.

The results are summarized in the following Table 4:

TABLE 4

| Test | $H_2O/CF_3COOK$ (% mol) | RC $CF_3CO_2K$ (%) | AY $CF_3CO_2K$ (%) | YC $CF_3CO_2K$ (%) |
|---|---|---|---|---|
| a | 1.9 | 67.2 | 27.9 | 41.5 |
| b | 2.3 | 64.2 | 43.2 | 67.3 |
| c | 3.9 | 65.3 | 44.2 | 67.8 |
| d | 6.9 | 69.4 | 39.6 | 57.1 |
| e | 8.9 | 69.1 | 39.9 | 57.7 |

In these tests, the formation of fluoride ions is observed with an AY yield of about 25%.

A marked improvement in the yield and the selectivity is observed on passing from conditions a) to b). An optimum appears within the range from 2 to 8%, around 4%.

EXAMPLE 9

This example summarizes a series of tests where fluoride ions were introduced into the reaction medium from the beginning of the reaction.

Test 9.a was carried out in NMP according to the procedure of Example 5, test d, and by adding 1 mole of potassium fluoride per mole of starting trifluorocarboxylic acid.

Tests 9.b–d were carried out in DMF according to the procedure of test 5.c and by adding various quantities of KF.

Tests 9.e, f, g were carried out in the same solvents using, this time, caesium fluoride.

The results are presented in the following Table 5:

TABLE 5

| Test | Solvent | Fluoride F$^-$/ CF$_3$CO$_2$K mol % | H$_2$O/ CF$_3$CO$_2$K mol % | RC CF$_3$CO$_2$K % | AY CF$_3$SO$_2$K % | YC CF$_3$SO$_K$ |
|---|---|---|---|---|---|---|
| 5.d | NMP | 0 | 1.7 | 67.1 | 27.9 | 41.5 |
| 9.a | " | KF 100 | 0.9 | 54.1 | 39.1 | 72.3 |
| 5.d | DMF | 0 | 1 | 73.5 | 41.8 | 56.9 |
| 9.b | " | KF 100 | 2 | 63.4 | 44.3 | 70 |
| 9.c | " | KF 10 | 1.4 | 73.8 | 45.9 | 62.2 |
| 9.d | " | KF 1 | 1.7 | 76 | 44.8 | 58.9 |
| 9.e | NMP | CSF 100 |  | 57.7 | 37.4 | 64.8 |
| 9.f | " | CSF 10 | 1.3 | 67.2 | 42.9 | 63.8 |
| 9.g | DMF | CSF 100 | 1.9 | 62.6 | 46.2 | 73.8 |

In all cases, the rate of conversion of CF$_3$CO$_2$K is limited by the presence of the fluorides and an increase is observed in the selectivity and, in general, the yields.

EXAMPLE 10

In this example, the results obtained in the absence and in the presence of a sequestering crown ether, 18-crown-6, are compared.

Different tests were performed in various solvents, according to the procedure of Example 6.

The results are summarized in the following table.

TABLE 6

| Test | Solvent | H$_2$O/CF$_3$CO$_2$K (mol %) | 18 Cr6/CF$_3$CO$_2$K (mol %) | RC (%) | AY CF$_3$SO$_2$K (%) | YC F$^-$ (%) | YC CF$_3$SO$_2$K (%) |
|---|---|---|---|---|---|---|---|
| 5.d | NMP | 1.9 | 0 | 67.2 | 27.9 | 25.1 | 41.5 |
| 10.a | NMP | 1.5 | 25 | 73.8 | 23.8 | 0 | 32.2 |
| 5.b | CH$_3$CN | 1.6 | 0 | 12.6 | 3 | 3 | 23.8 |
| 10.b | CH$_3$CN | 1.5 | 25 | 47.6 | 6.1 | 3 | 12.8 |
| 5.e | Benzonitrile | 1.5 | 0 | 22.1 | 7.4 | 3.6 | 33.5 |
| 10.c | Benzonitrile | 1.2 | 25 | 35.8 | 14.8 | 5.7 | 41.3 |
| 5.i | Xylene | 0.5 | 0 | 23.2 | 4.4 | 3 | 19 |
| 10.d | Xylene | 0.5 | 25 | 28.4 | 6.3 | 3 | 22.2 |

In all cases, the conversion of the starting product is favoured, without notable effect, however, on the decomposition into fluorides. This is even reduced with the NMP solvent.

In tests b, c and d, the actual yield of CF$_3$SO$_2$K is much better when the sequestrant is used.

EXAMPLE 11

This example presents a kinetic study of the reaction of test 5.d.

The rate of conversion of the trifluoroacetate, the actual yield and the yield of conversion of the trifluoromethylsulphinate as well as the actual yield of fluoride ion were determined for reaction times varying between 2 and 9 h 30 min.

The results are summarized in Table 7 below.

TABLE 7

| Test | Time (h) | H$_2$O/ CF$_3$CO$_2$K mol % | RC % | AY CF$_3$SO$_2$K % | AY F$^-$ % | YC CF$_3$SO$_2$K % |
|---|---|---|---|---|---|---|
| 11.a | 2 | 1.3 | 46.2 | 23.5 | 3 | 51 |
| 11.b | 4 | 1.2 | 52.7 | 42.1 | 3 | 79.9 |
| 5.d | 6 | 1.9 | 67.2 | 27.9 | 25.1 | 41.5 |
| 11.c | 9 h 30 min | 1.3 | 81.4 | 4.1 | 83.3 | 5 |

A maximum yield and a maximum selectivity are observed at around 4 h of reaction.

When the reaction time increases, the yield drops and an increasing quantity of fluoride ions appears, which is a sign of degradation of the trifluoromethyl groups in the medium.

EXAMPLE 12

Preparation of pentafluoroethylsulphinic acid 40 g of NMP, 7.07 g of anhydrous C$_2$F$_5$COOK (35 mmol) and 4.9 g (76 mmol) of SO$_2$ are introduced into the same reactor as that of Example 1.

The mixture is heated in the closed reactor at a temperature of 140° C. for 6 hours.

The pressure variation inside the reactor between the beginning and the end of the reaction is 3.5 bar.

The reaction medium is taken up in water and then the mixture is assayed by $^{19}$F NMR.

The rate of conversion RC is equal to 85%, the actual reaction yield AY is equel to 73% and the yield of conversion YC is equal to 86.2%. The product is isolated in the form of a potassium salt.

EXAMPLE 13

Preparation of heptafluoropropylsulphinic acid 40 g of NMP, 8.8 g of anhydrous C$_3$F$_7$COOK (35 mmol) and then 4.9 g (76 mmol) of SO$_2$ are introduced into the same reactor as that of Example 1.

The mixture is heated in the closed reactor at a temperature of 140° C. for 1 h 30 min.

The pressure variation inside the reactor between the beginning and the end of the reaction is 4.5 bar.

The reaction medium is taken up in water, then the mixture is assayed by $^{19}$F NMR.

The rate of conversion RC is equal to 85%, the actual reaction yield A is equal to 70% and the yield of conversion YC is equal to 82%.

The product is isolated in the form of a potassium salt.

EXAMPLE 14

Preparation of trifluoromethylsulphinyl chloride

Potassium trifluoromethylsulphinate is prepared under the conditions of Example 4.

The DMF is removed from the reaction mixture by vacuum distillation at a temperature not exceeding 55°–60° C.

The distillation residue is taken up in acetonitrile and then filtered. The filtrate is distilled in order to remove the solvent and the potassium trifluoromethylsulphinate is isolated with a purification yield of 96% relative to the crude reaction mixture, assayed by ionic chromatography.

The product resulting from this operation is taken up in toluene and supplemented with thionyl chloride $SOCl_2$ in a stoichiometric quantity relative to the trifluoromethylsulphinate. The trifluoromethylsulphinyl chloride ($CF_3SOCl$) is obtained with a yield of 65%.

EXAMPLE 15

Preparation of trifluoromethylsulphonyl chloride

Potassium trifluoromethanesulphinate is prepared under the conditions of Example 4.

The DMF is removed from the reaction mixture by vacuum distillation at a temperature not exceeding 60° C.

The distillation residue is taken up in water.

Chlorine is bubbled through the aqueous solution in a stoichiometric quantity relative to the trifluoromethylsulphinate present in the medium.

The reaction temperature is 0°–5° C.

By separating the bottom layer after settling has taken place, the trifluoromethylsulphonyl chloride is isolated.

This crude product is distilled, b.p.: 28°–31° C. The yield is 80% relative to the trifluoromethylsulphinate present in the medium.

EXAMPLE 16

Preparation of trifluoromethylsulphonic acid (triflic acid)

The aqueous solution obtained under the same conditions as those described in Example 15 is oxidized with hydrogen peroxide at 30 volumes. A 10% excess of hydrogen peroxide relative to the potassium trifluoromethylsulphinate is necessary.

The reaction temperature is 5° C.

After distillation of the water and drying, the salts obtained are acidified using 100% sulphuric acid. The triflic acid is thus separated from the trifluoromethylacetic acid.

We claim:

1. A process for the synthesis of a salt of an organic compound which is both fluorine-containing and oxysulphide-containing, comprising the steps of:
   a) forming a mixture of (1) a reagent comprising a fluorocarboxylic acid of formula Ew—$CF_2$—COOH where Ew is an electron-withdrawing group or atom which is at least partially salified by an organic or inorganic cation, and an aprotic polar solvent; and (2) an oxide of sulphur; and
   b) heating the resulting mixture at a temperature of between 100° C. and 200° C., for a period of between half an hour and 20 hours.

2. The process according to claim 1, wherein the said oxide of sulphur is sulphur dioxide.

3. The process according to claim 2, wherein the mixture of step a) is a liquid in equilibrium with a gaseous phase containing sulphur dioxide.

4. The process according to claim 1, wherein the reaction products are separated while the rate of conversion of the fluorocarboxylic acid is 40 to 80%.

5. The process according to claim 2, wherein a sulphinic acid salt is obtained in step b) and comprising a step c) of oxidizing the sulphinic acid salt by exposing the product of step b) to an oxidizing reagent.

6. The process according to claim 1, wherein the reagent has a proton content at most equal to 10% of the molar concentration of the said fluorocarboxylic acid.

7. The process according to claim 1, wherein the reagent has a water content less than 10% of the molar concentration of the said fluorocarboxylic acid.

8. The process according to claim 1, wherein the reagent has a content of transition elements having at least two stable valency states less than 1000 mol ppm, relative to the said fluorocarboxylic acid.

9. The process according to claim 1, wherein the reagent has a content of column VIII elements in the periodic classification of the elements less than 100 mol ppm, relative to the said fluorocarboxylic acid.

10. The process according to claim 1, wherein the content, expressed in equivalent, of said ionic fluoride is at most equal to the molar concentration of the said fluorocarboxylic acid.

11. The process according to claim 1, wherein the donor number of the said polar aprotic solvent is between 10 and 30.

12. The process according to claim 1, wherein the acceptor number of the said solvent is less than 20.

13. The process according to claim 1, wherein the pKa corresponding to the first acidity of the said solvent is at least equal to 20.

14. The process according to claim 1, which comprises a sequestering crown ether.

15. The process according to claim 1, wherein the said electron-withdrawing atom or group is selected from electron-withdrawing groups whose Hammet constant op is at least equal to 0.1.

16. The process according to claim 1, wherein the said acid is selected from the compounds of formula (1) X—$CF_2$—COOH, where X represents a halogen atom and the compounds of formula (2) R—G—$CF_2$—COOH, where R—G represents a nitrile group or alternatively G represents

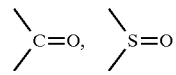

or —$(CF_2)_n$— with n greater than or equal to 1 and R is any organic or inorganic residue.

17. The process according to claim 1, wherein the said fluorocarboxylic acid, at least partially salified, is completely soluble in the reactive medium.

18. The process according to claim 1, wherein the said acid is salified by an alkali metal cation selected from sodium, potassium, rubidium, caesium and francium, or by a quaternary ammonium.

19. The process according to claim 1, wherein the solvent is selected from the N-disubstituted amides, including the tetrasubstituted ureas and the monosubstituted lactams, and the cyclic or noncyclic ethers, and benzonitrile.

* * * * *